United States Patent [19]

Takahashi et al.

[11] 4,071,553
[45] Jan. 31, 1978

[54] METHOD FOR THE PRODUCTION OF TRANS-4-AMINOMETHYL CYCLOHEXANE-1-CARBOXYLIC ACID

[75] Inventors: Masaaki Takahashi, Tokyo; Akira Iizuka, Higashimurayama; Kiro Asano, Kukizaki, all of Japan

[73] Assignee: Kureha Kagaku Kogyo Kabushiki Kaisha, Tokyo, Japan

[21] Appl. No.: 690,516

[22] Filed: May 27, 1976

[30] Foreign Application Priority Data

May 27, 1975 Japan ................... 50-62453

[51] Int. Cl.² .................. C07C 51/42; C07C 99/12
[52] U.S. Cl. ................................. 260/514 J
[58] Field of Search ........................ 260/514 J

[56] References Cited

FOREIGN PATENT DOCUMENTS 4,727,506  2/1972  Japan ........................ 260/514

*Primary Examiner*—Robert Gerstl
*Attorney, Agent, or Firm*—Lane, Aitken, Dunner & Ziems

[57] ABSTRACT

Disclosed is a method for producing trans-4-aminomethyl cyclohexane-1-carboxylic acid by heating and isomerizing cis-4-aminoethyl cyclohexane-1-carboxylic acid hydrochloride or a mixture of cis-4-aminomethyl cyclohexane-1-carboxylic acid hydrochloride with trans-4-aminomethyl cyclohexane-1-carboxylic acid hydrochloride in an atmosphere of hydrogen chloride gas and in the absence of a solvent.

2 Claims, 1 Drawing Figure

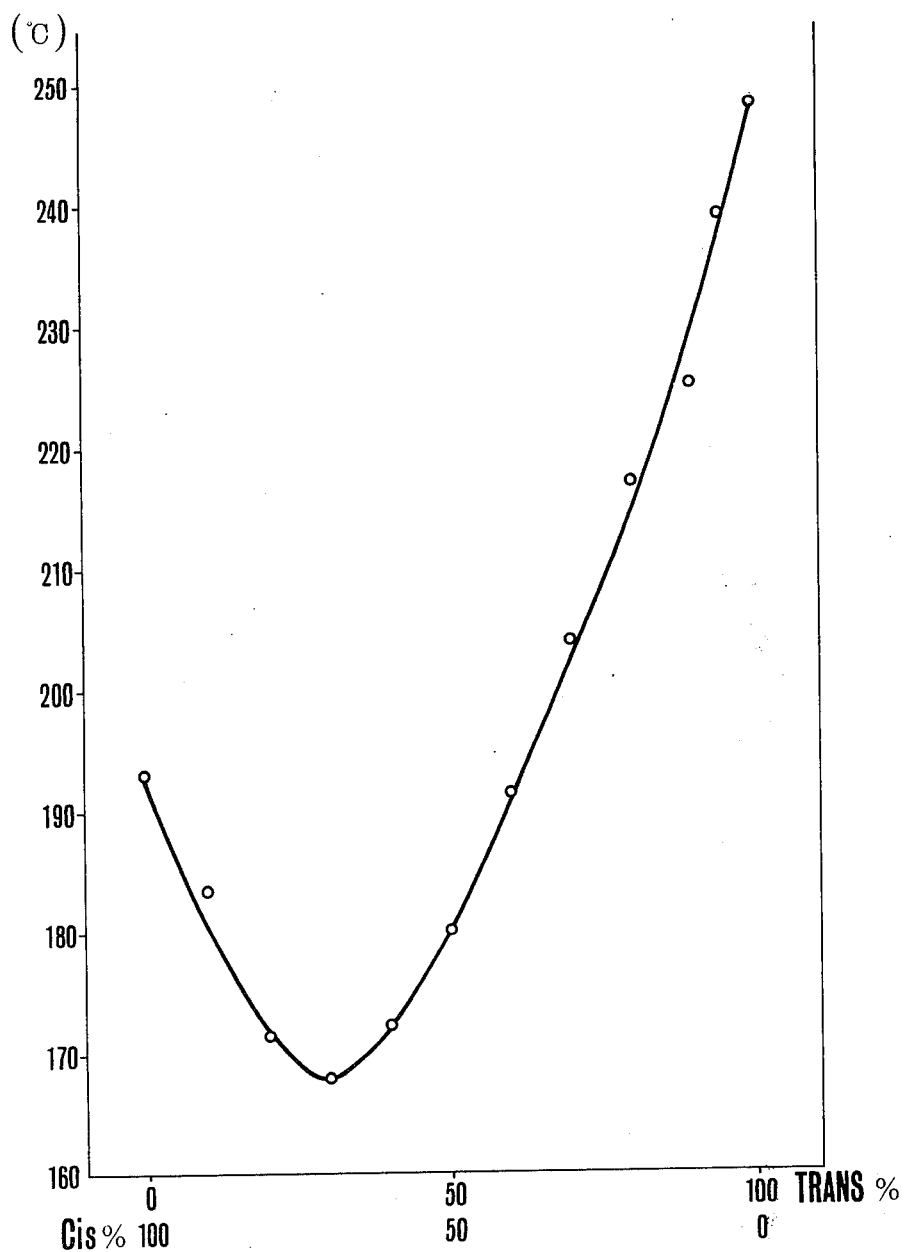

METHOD FOR THE PRODUCTION OF TRANS-4-AMINOMETHYL CYCLOHEXANE-1-CARBOXYLIC ACID

FIELD OF THE INVENTION

This invention relates to a novel method for the production of trans-4-aminomethyl cyclohexane-1-carboxylic acid.

BACKGROUND OF THE INVENTION

Trans-4-aminomethyl cyclohexane-1-carboxylic acid (hereinafter referred to as trans-AMCHA) has an antiplasmic activity and, therefore, is medicinally useful as an antiplasmic agent. For the production of trans-AMCHA, there have heretofore been proposed various methods such as (1) through (3) below.
1. A method for converting cis-4-aminomethyl cyclohexane-1-carboxylic acid (hereinafter referred to as cis-AMCHA) into trans-AMCHA by heating cis-AMCHA or a mixture of cis-AMCHA with trans-AMCHA (hereinafter referred to as cis-trans-AMCHA mixture) in water as the solvent in the presence of an alkali hydroxide, alkali carbonate or alkali hydrogen carbonate at temperatures in the range of from 160° C to 250° C under pressure (Japanese Patent Publication No. 14830/1966).
2. A method for converting cis-AMCHA into trans-AMCHA by heating cis-AMCHA or cis-trans-AMCHA mixture in water as the solvent in the presence of the hydroxide or oxide of an alkaline earth metal under pressure (Japanese Patent Publication No. 23018/1967).
3. A method for converting cis-AMCHA into trans-AMCHA by heating cis-AMCHA or cis-trans-AMCHA mixture in the presence of hydrochloric acid or sulfuric acid (Japanese Patent Publication No. 27506/1972).

In the conventional techniques described above, however, the trans-AMCHA products obtained thereby do not have high purity and are in the form of a mixture containing a fairly large proportion of cis-AMCHA (hereinafter this mixture will be referred to as trans-cis-AMCHA). In order to obtain trans-AMCHA of high purity suitable for medicinal use, it is necessary to separate trans-AMCHA from the trans-cis-AMCHA such as by one of the following methods (4) through (7) below.
4. A method which includes converting the trans component and the cis component of the trans-cis-AMCHA into respective paratoluene sulfonates and separating the trans component in the form of sulfonate by virtue of the difference in solubilities of the two paratoluene sulfonates (Japanese Patent Publications No. 28810/1968 and No. 16974/1968).
5. A method for isolatng trans-AMCHA in the form of a sulfate, iodate or sulfosalicylate (Japanese Patent Publication No. 27506/1972).
6. A method for isolating trans-AMCHA in the form of a phthalic acid or phthalate (Japanese Patent Publication No. 24893/1967).
7. A method for isolating trans-AMCHA in the form of a copper salt (Japanese Patent Publication No. 4784/1966).

In the production of trans-AMCHA of high purity, the conventional techniques have inevitably necessitated combination of an isomerization step for converting cis-AMCHA into trans-AMCHA and a separation step for isolating trans-AMCHA from the resultant trans-cis-AMCHA as described above. The techniques thus have the disadvantage that the operations involved are both time-consuming and complicated. In the production of trans-AMCHA of high purity, the conventional techniques also require an isomerization reaction to proceed in water as the solvent in the presence of an acid or alkali. Since this isomerization reaction is accompanied by secondary reactions as hydrolysis and polymerization, it is difficult for the conventional techniques to afford trans-AMCHA in high yields. Moreover, since the reaction vessels used for the isomerization reaction contain aqueous solutions of acids of alkalis at elevated temperatures under pressure, corrosion represents a serious problem. The conventional techniques, therefore, require for use in the isomerization process quite expensive vessels capable of withstanding the corroding action of the aqueous solutions.

SUMMARY OF THE INVENTION

It is, therefore, an object of the present invention to provide an advantageous method for the production of trans-AMCHA without entailing the various difficulties which are encountered by the conventional techniques as described above.

This object and the other objects of the present invention will become apparent from the following description.

Based on the assumption that trans-AMCHA would very easily produced without necessitating the aforementioned troublesome separation process if the isomerization reaction could be made to proceed efficiently, a study was made in search of a method capable of converting cis-AMCHA into trans-AMCHA in high yield. As a result it has been discovered that when cis-AMCHA hydrochloride or a mixture of cis-AMCHA hydrochloride with trans-AMCHA hydrochloride is thermally melted in an atmosphere of hydrogen chloride gas without a solvent, the cis-AMCHA hydrochloride is converted quite satisfactorily into trans-AMCHA hydrochloride.

This invention, thus, provides a method for the production of trans-AMCHA, which includes melting cis-AMCHA hydrochloride or a mixture of cis-AMCHA hydrochloride with trans-AMCHA hydrochloride in an atmosphere of hydrogen chloride gas to convert the cis-AMCHA hydrochloride into trans-AMCHA hydrochloride and subsequently dehydrochlorinating the trans-AMCHA hydrochloride.

BRIEF EXPLANATION OF THE DRAWING

The accompanying drawing is a diagram illustrating the phase equilibrium between the cis-AMCHA hydrochloride and trans-AMCHA hydrochloride.

DETAILED DESCRIPTION OF THE INVENTION

The cis-AMCHA hydrochloride used as the raw material in the present invention is the product of hydrochlorination of the cis-AMCHA which has heretofore been used as the raw material for the production of trans-AMCHA. Also the mixture of cis-AMCHA hydrochloride with trans-AMCHA hydrochloride, which is also used as a raw material in this invention, is similarly the product of hydrochlorination of the cis-trans-AMCHA mixture which has heretofore been used as the raw material for the production of trans-AMCHA.

This cis-trans-AMCHA mixture is generally obtained by the hydrogenation of p-aminomethylbenzoic acid and has a gravimetric cis/trans ratio of approximately from 8/2 to 6/4. The cis-AMCHA is, for example, a residue obtained when trans-AMCHA is separated from the trans-cis-AMCHA by the conventional technique.

As the first step, the present invention heats the cis-AMCHA hydrochloride or the mixture of cis-AMCHA hydrochloride with trans-AMCHA hydrochloride in an atmosphere of hydrogen chloride gas without a solvent at temperatures of from 160° C to 248° C exclusive, preferably from 170° C to 200° C, to convert the cis-AMCHA hydrochloride into trans-AMCHA hydrochloride. In this case, the heating can be carried out under pressure or in an open vessel. From the operational point of view, it is preferred to be performed under atmospheric pressure. In this reaction, the duration of heating is not particularly critical. For the isomerization reaction to proceed sufficiently, however, the heating is preferred to be continued for a period of about 5 to 20 hours. In order that the isomerization reaction may proceed to accomplish the conversion of cis-AMCHA hydrochloride into trans-AMCHA hydrochloride aimed at by this invention, the cis-AMCHA hydrochloride to be used as the raw material must be melted by heating at a temperature higher than the melting point thereof but lower than the melting point of the trans-AMCHA hydrochloride consequently produced. When a mixture of cis-AMCHA hydrochloride with trans-AMCHA hydrochloride is used as the raw material it must be melted by heating at a temperature higher than the melting point thereof but lower than the melting point of the trans-AMCHA hydrochloride consequently produced. As a result, the isomerization proceeds as a gas-liquid reaction to produce trans-AMCHA hydrochloride as a solid in the reaction system. The melting point of the cis-AMCHA hydrochloride and the azeotropic point of the mixture of cis-AMCHA hydrochloride with trans-AMCHA hydrochloride above which the melting of the raw material is effected are both higher than 160° C as shown in the attached diagram (the expression "temperatures higher than 160° C" taking into due consideration the melting point depression and the azeotropic point depression owing to the presence of impurities in the raw material). The melting point of the trans-AMCHA hydrochloride consequently produced is slightly lower than 250° C, namely about 248° C, as is evident from the attached diagram. In this graph, the horizontal axis is graduated for the proportion of components (percent by weight) and the vertical axis for the melting point (°C). For the purpose of the present invention, therefore, the temperature at which the heating is continued to effect the isomerization reaction must fall in the range of from 160° C to 248° C exclusive. When the cis-AMCHA or the cis-trans-AMCHA mixture which have previously been used as the raw material for the production of trans-AMCHA by the conventional techniques is used in the present invention, deamination results which in turn brings about an addition reaction and a polymerization reaction to the extent of impeding smooth progress of the isomerization reaction. In the present invention, therefore, either cis-AMCHA hydrochloride or a mixture of cis-AMCHA hydrochloride with trans-AMCHA hydrochloride must be used as the raw material.

The trans-AMCHA hydrochloride obtained by the reaction described above has a high purity of not less than 95%. If occasion demands, this trans-AMCHA hydrochloride may be refined such as by recrystallization to a purity of 99% or over. In the present invention, trans-AMCHA of high purity can be obtained by subsequently dehydrochlorinating the trans-AMCHA hydrochloride obtained as described above. The dehydrochlorination of the trans-AMCHA hydrochloride can be effected by an ordinary method. For example, it may be accomplished by dissolving the trans-AMCHA hydrochloride in water and passing the resultant aqueous solution through a bed of a basic ion-exchange resin.

As described above, the present invention permits trans-AMCHA of high purity to be produced very easily without the various drawbacks associated with the conventional techniques.

The present invention will be described more specifically below with reference to preferred embodiments. It should be noted that this invention is not in any way limited to these examples.

EXAMPLE 1

A glass ampoule was charged with 1 kg of powdered hydrochloride of cis-trans-mixed 4-aminomethyl cyclohexane-1-carboxylic acid (of which the gravimetric ratio of the cis component to the trans component was found through the gas chromatographic analysis of the N-acetylation product or butylesterification product thereof to be 65.9 : 34.1) and the air filling the remaining space of the glass ampoule was displaced with dry hydrogen chloride gas. This ampoule was hermetically sealed and then heated at 195° C for ten hours. After completion of the reaction, no change in the weight of the ampoule contents was detected. By analysis, the reaction product was found to contain substantially no secondary product. By gas chromatographic analysis, the gravimetric ratio of the trans component to the cis component of the product was found to be 97 : 3. The reaction product was dissolved in about 1.5 liters of water and the resultant aqueous solution was concentrated under reduced pressure to produce crystals. The crystals were found to have a melting point of 247°–248° C and the gravimetric ratio of trans component to cis component of the crystals was shown to be 99.5 : 0.5.

Trans-4-aminomethyl cyclohexane-1-carboxylic acid having a purity of 99.8% was obtained by again dissolving the crystals in about 10 liters of water, dehydrochlorinating the crystals by passing the resultant aqueous solution through a bed of a weakly basic ion-exchange resin (Amberlite IR-45 made by Rohm and Haas Company) and crystallizing the eluate by concentration under reduced pressure.

EXAMPLE 2

A glass ampoule was charged with 1 kg of powered hydrochloride of cis-trans-mixed 4-aminomethyl cyclohexane-1-carboxylic acid (of which the gravimetric ratio of the cis component to the trans component was found to be 65.9 : 34.1) and the air filling the remaining space in the glass ampoule was displaced with dry hydrogen chloride gas. The glass ampoule was hermetically sealed and heated at 185° C for 15 hours. After completion of the reaction, no change in the weight of the ampoule contents was detected. By analysis, the reaction product was found to contain substantially no secondary product and the gravimetric ratio of the trans component to the cis component of the product was found to be 97.2 : 2.8. This reaction product was dissolved in about 1.5 liters of water and the resultant aqueous solution was concentrated under reduced pressure to produce crystals. The melting point of the crystals was found to be 247°–248° C and the gravimetric ratio of the trans component to the cis component of the crystals to be 99.5 : 0.5.

Trans-4-aminomethyl cyclohexane-1-carboxylic acid having a purity of 99.7% was obtained by dissolving the crystals again in about 10 liters of water, dehydrochlorinating the crystals by passing the resultant aqueous solution through a bed of weakly basic ion-exchange resin (Amberlite IR-45 made by Rohm and Haas Company) and crystallizing the eluate by concentration under reduced pressure.

EXAMPLE 3

A glass cylindrical container was charged with 200 g of powdered hydrochloride of cis-trans-mixed 4-aminomethyl cyclohexane-1-carboxylic acid (of which the gravimetric ratio of the cis component to the trans component was found to be 65.9 : 34.1). It was heated at 195° C for ten hours under atmospheric pressure (with the container kept uncovered), with dry hydrogen chloride gas fed continuously to sweep the reaction system. After completion of the reaction, no appreciable change was found to have occurred in the weight of the contents. By analysis, the reaction product was found to contain substantially no secondary reaction product and the gravimetric ratio of the trans component to the cis component of the product was found to be 96 : 4.

Crystals were obtained by dissolving this reaction product in about 300 ml of water and concentrating the resultant aqueous solution under reduced pressure. The melting point of the crystals was found to be 247°–248° C and the gravimetric ratio of the trans component to the cis component was found to be 99.4 : 0.6.

Trans-4-aminomethyl cyclohexane-1-carboxylic acid having a purity of 99.6% was obtained by dissolving the crystals again in about 2 liters of water, dehydrochlorinating the crystals by passing the resultant aqueous solution through a bed of weakly basic ion-exchange resin (Amberlite IR-45 made by Rohm and Haas Company) and crystallizing the eluate through concentration under reduced pressure.

EXAMPLE 4

A small test tube (13 mm in diameter and 122 mm in length) was charged with 3.1 g of powdered hydrochloride of cis-trans-mixed 4-aminomethyl cyclohexane-1-carboxylic acid (of which the gravimetric ratio of the cis component to the trans component was found to be 65.9 : 34.1). The tube was placed in a larger test tube (30 mm in diameter and 250 mm in length). The reaction system was heated at 190° C for ten hours under atmospheric pressure (with the tubes unstopped, with dry hydrogen chloride gas continuously fed to sweep the reaction system. At the end of the reaction, the reaction product was pulverized to afford 3.0 g of white powder. This product had a melting point of 238°–240° C. By gas chromatographic analysis, it was found to contain the trans component by 97% by weight. Then, trans-4-aminomethyl cyclohexane-1-carboxylic acid having a purity of 99% was obtained by dissolving the product (hydrochloride) in 30 ml of water, dehydrochlorinating the product by passing the resultant aqueous solution through a bed of weakly basic ion-exchange resin (Amberlite IR-45 made by Rohm and Haas Company), concentrating the eluate under reduced pressure and reprecipitating the concentrated eluate with acetone.

EXAMPLE 5

In the same test-tube type reaction system as used in Example 4, 3.3 g of powdered hydrochloride of cis-trans-mixed 4-aminomethyl cyclohexane-1-carboxylic acid (of which the gravimetric ratio of the cis component to the trans component was found to be 47 : 53) was heated in the atmosphere of hydrogen chloride gas at 190° C for ten hours under atmospheric pressure. At the end of the reaction, the reaction product was pulverized to produce 3.2 g of white powder. It was found to have a melting point of 239°–241° C and contain 97% by weight of trans component. By treating this product (hydrochloride) in the same manner as in Example 4, there was obtained trans-4-aminomethyl cyclohexane-1-carboxylic acid having a purity of 99%.

What is claimed is:

1. A method for the production of trans-4-aminomethyl cyclohexane-1-carboxylic acid, which comprises:
    a. thermally melting cis-4-aminomethyl cyclohexane-1-carboxylic acid hydrochloride or a mixture of cis-4-aminomethyl cyclohexane-1-carboxylic acid hydrochloride and trans-4-aminomethyl cyclohexane-1-carboxylic acid hydrochloride without a solvent in an atmosphere of hydrogen chloride gas at a temperature in the range of from 160° C to 248° C, to convert the cis-4-aminomethyl cyclohexane-1-carboxylic acid hydrochloride into trans-4-aminomethyl cyclohexane-1-carboxylic acid hydrochloride; and
    b. subsequently dehydrochlorinating the trans-4-aminomethyl cyclohexane-1-carboxylic acid hydrochloride.

2. The method according to claim 1, wherein said temperature is are in the range of from 170° C to 200° C.

* * * * *